(12) United States Patent
Satoh et al.

(10) Patent No.: US 7,151,956 B2
(45) Date of Patent: Dec. 19, 2006

(54) IMAGING APPARATUS AND AN IMAGING HEAD USED THEREFOR

(75) Inventors: Masao Satoh, Saitama (JP); Makoto Toyota, Saitama (JP); Yasuo Shirai, Chiba (JP)

(73) Assignee: Moritex Corporation, Tokyo (JP)

( * ) Notice: Subject to any disclaimer, the term of this patent is extended or adjusted under 35 U.S.C. 154(b) by 219 days.

(21) Appl. No.: 10/192,500

(22) Filed: Jul. 11, 2002

(65) Prior Publication Data

US 2003/0012461 A1    Jan. 16, 2003

(30) Foreign Application Priority Data

Jul. 12, 2001    (JP)    ............... 2001-212788

(51) Int. Cl.
*A61B 6/00*    (2006.01)
(52) U.S. Cl. .............. 600/476; 600/407; 600/473; 600/474; 600/475; 600/477; 600/478; 600/129; 600/160
(58) Field of Classification Search ............... 600/407, 600/473–478, 129, 160; 250/317–345
See application file for complete search history.

(56) References Cited

U.S. PATENT DOCUMENTS

| 5,261,410 A | * | 11/1993 | Alfano et al. ............... 600/475 |
| 5,293,872 A | * | 3/1994 | Alfano et al. ............... 600/475 |
| 6,346,101 B1 | * | 2/2002 | Alfano et al. ............... 606/15 |
| 6,364,829 B1 | * | 4/2002 | Fulghum ............... 600/160 |
| 6,370,422 B1 | * | 4/2002 | Richards-Kortum et al. ............... 600/478 |
| 6,485,413 B1 | * | 11/2002 | Boppart et al. ............... 600/160 |

FOREIGN PATENT DOCUMENTS

| JP | 8-125891 | 5/1996 |
| JP | 3001165 | 11/1999 |

* cited by examiner

*Primary Examiner*—Brian L. Casler
*Assistant Examiner*—William Jung
(74) *Attorney, Agent, or Firm*—Greenblum & Bernstein, P.L.C.

(57) ABSTRACT

An imaging apparatus in which an imaging head having an observation hole for intaking images of an object to be observed formed at a top end is exchangeably mounted to a main body having an imaging device and an illumination light source wherein the imaging head is provided with a plurality of optical fibers for guiding a light from the illumination light source and illuminating the same to the object, light incident ends of respective optical fibers are disposed at positions opposing to emission ends of the illumination light source, and the light emission ends are circularly disposed around the image pick-up optical axis, whereby an appropriate illumination light in accordance with a magnifying ratio can be illuminated without disposing an illumination light source such as of LEDs to an imaging head such as an exchangeable lens unit.

20 Claims, 2 Drawing Sheets

IMAGING APPARATUS AND AN IMAGING HEAD USED THEREFOR

BACKGROUND OF THE INVENTION

1. Field of the Invention

This invention concerns an imaging apparatus for observing the surface of an object to be observed, which is particularly suitable to a magnifying imaging apparatus for observing skins or scalps of users under magnification in a case where cosmetic salesstuffs decide cosmetics or shampoos or rinses optimal to the users in accordance with conditions of users skins or scalps.

2. Related Art Statement

Recently, various measuring instruments and diagnostic instruments have been introduced not only in cosmetic counters of department stores but also in cosmetic stores in shopping streets.

Among all, magnifying observation apparatus such as CCD microscopes have become important as sales promotion aids since they can display skins to such a high magnification ratio as can not be seen usually, and salesstuffs can explain users while displaying, on a monitor, images of fine textures of skins formed by fine lines running in various directions, stains and freckles and roughened state of skins.

By the way, when skins are observed, the magnification ratio has to be changed depending on an object to be observed. For example, in a case of observing fine skin textures formed by fine lines running in various directions, it is preferred to pick-up images for a range of 1 to 2 cm diameter at a relatively low magnification ratio. On the other hand, in a case of closely observing individual textures, it is preferred to pick-up images for an extremely defined area of 1 to 2 mm diameter at a high magnification ratio.

Then, images in a range for 1 to 2 cm diameter can be picked-up by using a lens at a magnification ratio of about 20 and those in a range for 1 to 2 mm diameter can be picked-up by using a lens at a magnification ratio of about 200. The amount of light per unit area required for picking-up images is different between the magnification ratios 20 and 200.

Accordingly, as shown in FIG. 3, in an existent imaging apparatus 41, a main body 43 having an imaging device 42 for picking-up images of an object is mounted with an exchangeable lens unit 45 having a magnifying lens 44 at an optional magnification ratio, main body 43 is formed with a power supply contact 46, and white LEDs 47, 47, - - - that emit light upon receiving electric power from the contacts 46 are arranged circularly to each lens unit 45.

With the constitution described above, since the number, the kind and the attaching position of the light emitting device 47 can be designed optionally in accordance with the magnification ratio of the lens 44, an appropriate illumination light can be applied to the object in accordance with the magnification ratio.

However, when a plurality of white LEDs 47, - - - are arranged circularly on every exchangeable lens unit 45, it results in a problem of increasing the cost for manufacturing the exchangeable lens unit 45.

Further, in LEDs 47, - - - in the light emitting region of 1 to 2 mm diameter, the outer diameter of the casing thereof is about 3 to 4 mm. Then, even when they are arranged circularly in close contact to the each other with no gaps, a gap is inevitably formed between each of the adjacent light emitting regions.

Assuming a case where LEDs 47, - - - are circularly arranged in a narrow exchangeable lens unit 45, since the number of LEDs 47 is utmost 9 to 12, the angle of center thereof is 30 to 40° and each of the LEDs 47, - - - is imaged as a bright spot to the object when the magnification ratio is high.

For example, in a case of observing individual textures of skins at a high magnification ratio, since light of the LEDs 47, - - - is reflected as the bright spot at the edges as the boundaries between cutaneous trenches and protrusions, the edges can not be imaged clearly.

Further, lights of three primary colors are illuminated substantially uniformly from the white LED 47 but, since lights for respective colors are not completely overlapped with each other, when the lights from the LEDs 47, 47, - - - are illuminated directly to an object, the illumination light is spectralized into three colors at the peripheral edge of the illumination spot to result in a problem that images are difficult to be seen.

In view of the above, this invention intends to illuminate an appropriate illumination light in accordance with a magnification ratio to an object to be observed without providing an illumination light source such as LEDs to an imaging head such as an exchangeable lens unit, and with no polarization and with no reflection of bright spots.

SUMMARY OF THE INVENTION

In view of the above, this invention provides an imaging apparatus in which a imaging head having an observation hole for intaking an image of an object to be observed formed at a top end is mounted exchangeably to a main body having an imaging device and an illumination light source, wherein the imaging head is provided with a light guide for guiding a light from the illumination light source and illuminating the same to the object, light incident ends of the light guide are disposed at positions opposing to light emission ends of the illumination light source, while the light emission ends are disposed circularly around an image pick-up optical axis.

According to this invention, a light illuminated from the illumination light source such as LEDs disposed to the main body enters into a plurality of optical fibers disposed to the imaging head and then illuminated from the emission ends thereof to an object to be observed.

In a preferred embodiment of this invention in which a bundle of fibers formed by bundling optical fibers at light incident ends is used and light emission ends are branched into each of fiber and arranged circularly around an image pick-up optical axis, the light of the illumination light source, even when the number thereof is small, can be reliably entered into the bundle of fibers and illuminated in a ring-pattern.

In a further embodiment of this invention, in which an imaging head is an exchangeable lens unit having lenses that intakes images of an object to be observed under magnification, contraction or at an equi-ratio as it is, the light emission ends of the optical fibers are disposed at optimal position in accordance with the magnification/contraction ratio of the lens.

Then, when the light emission ends are arranged circularly with no gaps, since each of the optical fibers is extremely fine, ring-pattern light is illuminated from the light emission ends and the light is not imaged as bright spot to the images of the object.

Further, also in a case of using white LEDs as the illumination light source, since lights for respective colors of different wavelengths are subjected to mode dispersion when they pass through the optical fibers and they are mixed at the light emission end face, the lights are illuminated as a white light with no color shading on the object to be observed with no spectralization of lights of respective colors.

Further, since there is no requirement for providing an illumination light source such as LEDs to the imaging head, the manufacturing cost can be reduced.

DESCRIPTIONS OF THE ACCOMPANYING DRAWINGS

EMBODIMENT OF THE INVENTION

Figure 1:
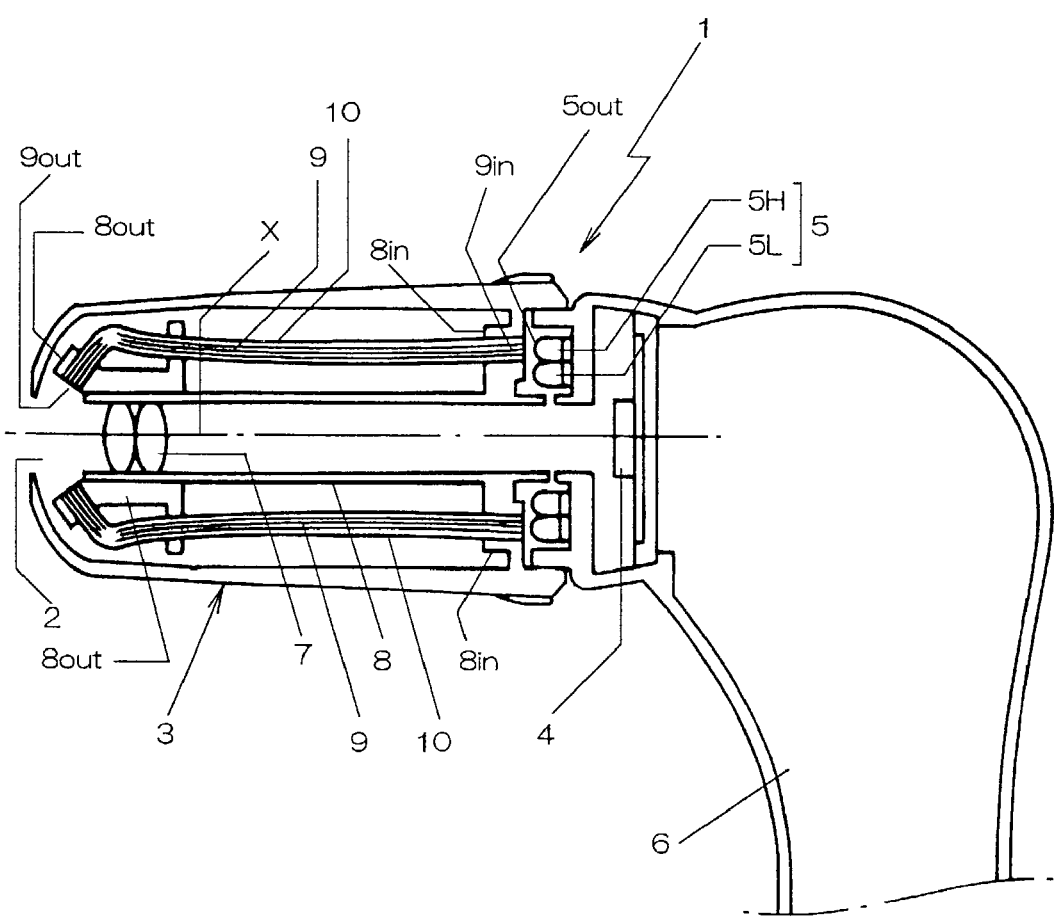
FIG. 1 is a schematic constitutional view showing an imaging apparatus and an imaging head according to this invention.
Figure 2:
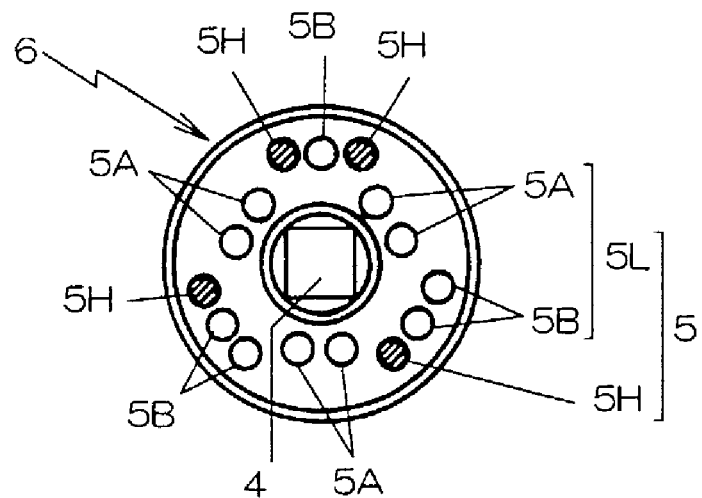
FIG. 2 is an explanatory view showing an illumination light source.
Figure 3:
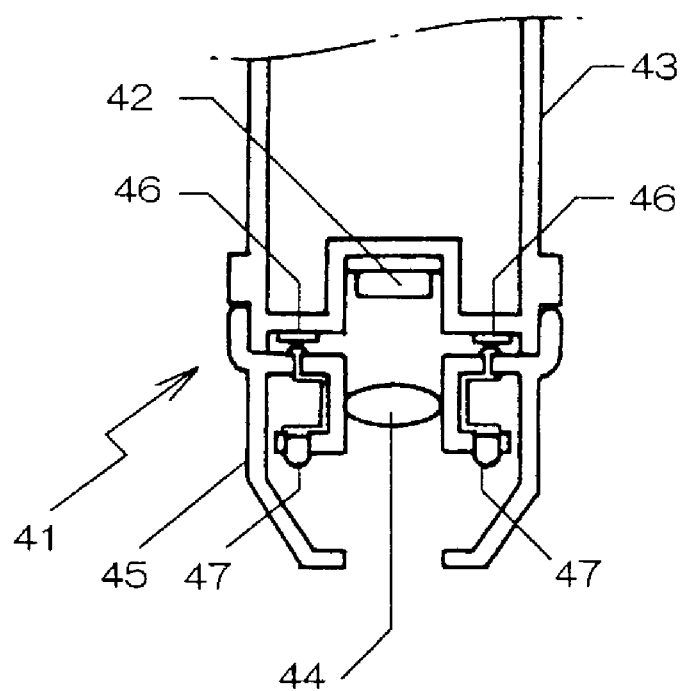
FIG. 3 is an explanatory view showing an existent apparatus.

Preferred embodiments of this invention will be explained specifically with reference to the drawings.

An imaging apparatus 1 of this embodiment has an imaging head 3 formed with an observation hole 2 for intaking images of an object to be observed at a top end, and the imaging head is mounted exchangeably to a main body 6 having an imaging device 4 such as a CCD device or C-MOS device and an illumination light source 5.

The illumination light source 5 comprises white LEDs at high brightness by the number of six at the inside and by the number of nine arranged circularly at the periphery of the imaging device 4. White LEDs comprising six elements at the inside and five elements at the outside are illumination light sources 5L for low magnification ratio and the remaining four white LEDs at the outside are illumination light sources 5H for high magnification ratio in which the front ends of respective white LEDs constitute the light emission ends 5out.

In the illumination light sources 5L for low magnification ratio, six white LEDs at the inside are light sources SA for subcutaneous observation and five light sources at the outside are light sources 5B for surface observation.

The imaging head 3 has a lens 7 for intaking images of the object under magnification at a predetermined ratio (for example several hundreds) disposed along an image pick-up optical axis X from the observation hole 2 to the imaging device 4 and the head is used as an exchangeable lens unit.

The lens 7 is used not only in a case of magnifying images of an object, but also in a case of picking-up images of the object under contraction or at an equi-ratio, as well as in a case of picking-up images covered with an optional special filter.

Flanges 8in and 8out are formed on both of front and rear ends of a substantially cylindrical lens holder 8 that hold the lens 7 for holding a plurality of optical fibers 9, 9, - - - that guide the light of the illumination light sources 5H for high magnification ratio and irradiate the light to the object.

The optical fibers 9, 9, - - - are bundled at light incident ends 9in into a bundle of fibers 10 in which respective light incident ends 9in for four bundle of fibers 10 are disposed at positions opposing to the emission ends 5out of respective white LEDs of the illumination light sources 5H for high magnification ratio and fixed to the flange 8in.

Further, the light emission ends 9out are branched into each of optical fibers 9, which are arranged circularly with no gaps at the flange 8out, so that ring-pattern illumination light can be illuminated conically at a predetermined angle of illumination toward the center of the observation hole 2.

As the imaging head for low magnification ratio, a head having no optical fibers 9, and illuminating the light of the illumination light sources 5L for low magnification ratio disposed to the main body 6 directly to an object to be observed may also be used.

The example of the constitution for the invention is as has been described above and the operation thereof is to be explained in a case of picking-up images at high magnification ratio, At first, the imaging head 3 for high magnification ratio is mounted to the main body 6, and the observation hole 2 is placed on an object to be observed such as a skin surface. When the illumination light sources 5H for high-magnification ratio is lit, the illumination light enters to the light incident ends 9in of the bundle of fibers 10 disposed being opposed to the light emission ends 5out of the respective LEDs, and then illuminated from the light emission ends 9out arranged circularly with no gaps at the flange 8out toward the center of the observation hole 2 conically at a predetermined angle of illumination.

In this case, since the light emission ends 9out can be arranged closer to the object, the light of the illumination light sources 5H for high magnification ratio can be spot-illuminated efficiently only to the imaging area even when the magnification ratio of the lens 7 is high, so that bright illumination necessary and sufficient for picking-up images at high magnification illumination can be obtained.

Accordingly, even when the illumination light sources are not disposed to the imaging head 3, illumination light capable of coping with image pick-up at high magnification ratio can be illuminated and manufacturing cost of the head can be reduced.

Further, since the ring-pattern light is illuminated conically toward the center of the observation hole 2, the illumination light is illuminated uniformly with the imaging area of the object as a center from all directions thereof, and the lights are not imaged as bright spots to the images of the object.

Further, even when white LEDs are used as the illumination light sources 5H, lights of respective colors of different wavelengths are put to mode dispersion when they pass through the inside of the optical fibers and sufficiently mixed at the light emission ends 9out, so that they are illuminated as a white light with no color shading to the object.

In the foregoing descriptions, while explanations have been made to a case of disposing LEDs at the periphery of the imaging device 4 as the illumination light sources disposed to the main body 6, LEDs may also be disposed to the inside of the main body 6 and the light may be guided through the optical fibers as far as the periphery of the imaging device 4 and the light emission ends of the optical fibers may be used as the light emission ends 5out. In summary, they may be constituted optionally so long as the light emission ends 5out are formed being opposed to the light incident ends 9in of the optical fibers 9 disposed to the imaging head 3.

As has been described above, according to this invention, since the light illuminated from the illumination light sources disposed to the main body is guided by way of the optical fibers disposed to the imaging head as far as the vicinity of the observation hole and then illuminated from the light emission ends to the object to be observed, this can provide an excellent effect capable of illuminating an appropriate illumination light in accordance with a magnification ratio, without causing color shading and not reflecting bright spots.

The present disclosure relates to subject matter contained in priority Japanese Patent Application No.2001-212,788 filed on Jul. 12, 2001, the contents of which is herein expressly incorporated by reference in its entirety.

What is claimed is:

1. An imaging apparatus in which an imaging head having an observation hole for receiving images of an object to be observed is provided at a top end and is exchangeably mounted to a main body having an imaging device and an illumination light source wherein the imaging head is provided with a plurality of optical fibers that guide light from the illumination light source and transmit the light to illuminate the object, light incident ends of the plurality of optical fibers being disposed at positions opposite emission ends of the illumination light source, and the light emission ends of the plurality of optical fibers are circularly disposed around an image pick-up optical axis;

the illumination light source comprises a first illumination light that allows observation by a low magnification ratio and a second illumination light that allows observation by a high magnification ratio; and the first illumination light comprises inside and outside light sources, wherein the inside light source allows subcutaneous observation and is disposed radially inward of the outside light source that allows surface observation.

2. An imaging apparatus as defined in claim 1, wherein the light incident ends of respective optical fibers are disposed at positions opposite the light emission ends of the second illumination light including the high magnification ratio.

3. The imaging apparatus according to claim 1, wherein the optical fibers extend conically toward the center of the observation hole.

4. The imaging apparatus according to claim 1, wherein the illumination light source is arranged about a periphery of the imaging device.

5. An imaging head having an observation hole for receiving images of an object to be observed is provided at a top end, the imaging head being configured to be exchangeably mounted to a main body having an imaging device and an illumination light source, wherein a plurality of optical fibers that guide light from the illumination light source and that transmit light to illuminate an object to be observed, the light incident ends of the plurality of optical fibers are disposed at positions opposite the light emission ends of the illumination light source, and the light emission ends of the plurality of optical fibers are disposed circularly around an image pick-up optical axis;

the illumination light source comprises a first illumination light that allows observation by a low magnification ratio and a second illumination light that allows observation by a high magnification ratio; and the first illumination light comprises inside and outside light sources, wherein the inside light source allows subcutaneous observation and is disposed radially inward of the outside light source, which allows surface observation.

6. An imaging head as defined in claim 5, wherein the light incident ends of the plurality of optical fibers are disposed at positions opposite the light emission ends of the second illumination light including the high magnification ratio.

7. An imaging head as defined in claim 6, wherein one or more bundle of fibers comprise the plurality of optical fibers, the bundle of fibers being bundled at the light incident ends and branched into each of the optical fibers at the light emission ends.

8. An imaging head as defined in claim 7, wherein a lens for receiving images of an object to be observed is disposed on an image picking-up optical axis and constituted as an exchangeable lens unit.

9. An imaging head as defined in claim 6, wherein a lens for receiving images of an object to be observed, is disposed on an image picking-up optical axis and comprises an exchangeable lens unit.

10. An imaging head as defined in claim 5, wherein one or more bundle of fibers comprise the plurality of optical fibers, the bundle of fibers being bundled at the light incident ends and branched into each of the optical fibers at the light emission ends.

11. An imaging head as defined in claim 10, wherein a lens for receiving images of an object to be observed is disposed on an image picking-up optical axis and comprises an exchangeable lens unit.

12. An imaging head as defined in claim 5, wherein a lens for receiving images of an object to be observed is disposed on an image picking-up optical axis and comprises an exchangeable lens unit.

13. The imaging apparatus according to claim 5, wherein the optical fibers extend conically toward the center of the observation hole.

14. An imaging apparatus in which an imaging head, having an observation aperture, is exchangeably mounted to a main body having an imaging device and an illumination light source, wherein the imaging head including a plurality of optical fibers that direct light from the illumination light source towards the object, light incident ends of the plurality of optical fibers being disposed at positions opposite emission ends of the illumination light source, and the light emission ends of the plurality of optical fibers are disposed about an image pick-up optical axis;

the illumination light source comprises a first illumination light that allows observation by a low magnification ratio and a second illumination light that allows observation by a high magnification ratio; and the first illumination light comprises inside and outside light sources, wherein the inside light source allows subcutaneous observation and is disposed radially inward of the outside light source, which allows surface observation.

15. The imaging apparatus according to claim 14, wherein the optical fibers extend conically toward a center of the observation aperture.

16. The imaging apparatus according to claim 14, wherein the light incident ends of each of the optical fibers are disposed at positions opposite the light emission ends of the second illumination light including the high magnification ratio.

17. An imaging head according to claim 14, wherein one or more bundle of fibers comprises the plurality of optical fibers, the bundle of fibers being bundled at the light incident ends and branched into each of the optical fibers at the light emission ends.

18. An imaging head according to claim 14, wherein a lens to observe an object is disposed on an image pick-up optical axis and comprises exchangeable lens unit.

19. The imaging apparatus according to claim 14, wherein the illumination light source is arranged about a periphery of the imaging device.

20. The imaging apparatus according to claim 14, wherein the light emission ends of the optical fibers direct light towards the optical axis of the image pick-up.

* * * * *